United States Patent
Bueno et al.

(10) Patent No.: US 6,466,643 B1
(45) Date of Patent: Oct. 15, 2002

(54) HIGH SPEED DIGITAL RADIOGRAPHIC INSPECTION OF AIRCRAFT FUSELAGES

(75) Inventors: Clifford Bueno, Clifton Park, NY (US); Kenneth Gordon Herd, Niskayuna, NY (US); Gregory Alan Mohr, Scotia, NY (US); Thomas James Batzinger, Burnt Hills, NY (US); Dennis Michael Walsh, Southlake, TX (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/643,688

(22) Filed: Aug. 22, 2000

Related U.S. Application Data

(60) Provisional application No. 60/175,089, filed on Jan. 7, 2000.

(51) Int. Cl.[7] ............................................... G01B 15/06
(52) U.S. Cl. .......................................... 378/58; 378/59
(58) Field of Search ............................. 378/58, 59, 197

(56) References Cited

U.S. PATENT DOCUMENTS

| | | | | |
|---|---|---|---|---|
| 3,835,324 A | * | 9/1974 | Weigle | 250/360 |
| 3,911,733 A | * | 10/1975 | Bhuta et al. | 73/88 |
| 4,078,180 A | * | 3/1978 | Green | 250/358 |
| 4,976,136 A | | 12/1990 | Willan | 73/40.7 |
| 5,014,293 A | * | 5/1991 | Boyd et al. | 378/197 |
| 5,083,451 A | | 1/1992 | Kling | 73/49.2 |
| 5,237,598 A | | 8/1993 | Albert | 378/99 |

OTHER PUBLICATIONS

Siegel, Mel, "Remoted and Automated Inspection: Status and Prospects," Proceedings of The First Joint DoD/FAA/NASA Conference on Aging Aircraft, Odgen, Utah, Jul. 8–10, 1997, pp. 859–872.

Aircraft Inspection with a Portable, Filmless XRay System Using Reverse Geomtry, by Richard Albert, William Pember, Jeff Garrison, and David Reyna, Materials Evaluation, May, 2000, pp. 643, 644, 645.

* cited by examiner

*Primary Examiner*—David P. Porta
*Assistant Examiner*—Irakli Kiknadze
(74) *Attorney, Agent, or Firm*—V. G. Ramaswamy; Pierce Atwood, Attorneys

(57) ABSTRACT

A system and method for radiographic inspection of aircraft fuselages includes a radiation source preferably located inside of the fuselage and a radiation detector preferably located outside of the fuselage. A source positioning system is provided for moving the radiation source longitudinally with respect to the fuselage, and a detector positioning system is provided for positioning the radiation detector in longitudinal alignment with the radiation source. The detector positioning system also moves the radiation detector circumferentially with respect to the fuselage. In operation, the radiation detector is moved over the fuselage in a circumferential direction while the radiation source illuminates an adjacent region of the fuselage with radiation.

30 Claims, 4 Drawing Sheets

HIGH SPEED DIGITAL RADIOGRAPHIC INSPECTION OF AIRCRAFT FUSELAGES

CROSS REFERENCE TO RELATED APPLICATION

This application claims the benefit of U.S. Provisional Application Ser. No. 60/175,089, filed Jan. 7, 2000.

BACKGROUND OF THE INVENTION

This invention relates generally to radiographic inspection and more particularly to high speed digital radiography for inspecting aircraft fuselages.

An aircraft fuselage typically comprises a grid of circumferential frame members and longitudinal stringers covered by a skin of lightweight sheet metal. The skin is ordinarily attached to the frame members and stringers by means of rivets or the like. To ensure passenger comfort at high altitudes, aircraft are provided with cabin pressurization systems that produce near sea-level air pressure breathing environments in the aircraft cabin. The application of cabin pressure causes the skin, frame members and stringers to expand slightly. When the pressure is removed, the skin, frame members and stringers return to their normal shape. Although the pressure differentials involved are relatively small, the repeated cycles of stress imposed on the fuselage structure by the pressurization and depressurization sequence that occurs during each flight can lead to fatigue and crack formation. This fatigue damage is often assisted by corrosion of the fuselage structures.

Fatigue cracks by nature can be extremely small in size and difficult to detect. The cracks are normally so small that routine pressurization of the aircraft cabin will not result in detection because the tiny cracks will not cause a detectable pressure loss in the aircraft. The combined effect of corrosion and cyclic stress can also cause looseness around the rivets and/or rivet cracking. If not detected, this condition could result in skin separation from the frame members and stringers.

Traditionally, aircraft fuselage inspection relies largely on visual inspection techniques. These techniques require extensive disassembly of the aircraft, including removal of objects such as overhead bins, interior panels, insulation and the like. This approach is thus time consuming, labor intensive and expensive. Furthermore, visual inspection techniques rely heavily on human ability and are limited by ambient lighting conditions, environmental effects, and the inspector's physical and mental limitations such as eye vision corrections, time constraints, mental attitude, concentration and judgment.

Radiography is another approach to aircraft fuselage inspection that has been proposed. However, using radiographic film to capture images of the fuselage is a costly, labor intensive process typically requiring large amounts of film. It is also a relatively slow process as the film must be removed and developed before the images can be examined. Replacing the film with an X-ray detector capable of providing electronic images is an alternative to X-ray film, but systems of this sort generally require precise alignment of the X-ray source and detector with respect to each other and the fuselage. This alignment has been heretofore difficult to achieve given the immense size of aircraft fuselages.

Accordingly, it would be desirable to have a method and apparatus capable of performing high speed digital radiographic inspection of aircraft fuselages without removal of interior bins, panels, insulation, lights, wiring and so on.

BRIEF SUMMARY OF THE INVENTION

The above-mentioned need is met by the present invention, which provides a system and method for radiographic inspection of aircraft fuselages in which a radiation source is preferably located inside of the fuselage, and a radiation detector is preferably located outside of the fuselage. A source positioning system is provided for moving the radiation source longitudinally with respect to the fuselage, and a detector positioning system is provided for positioning the radiation detector in longitudinal alignment with the radiation source. The detector positioning system also moves the radiation detector circumferentially with respect to the fuselage. In operation, the radiation detector is moved over the fuselage in a circumferential direction while the radiation source illuminates an adjacent region of the fuselage with radiation.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
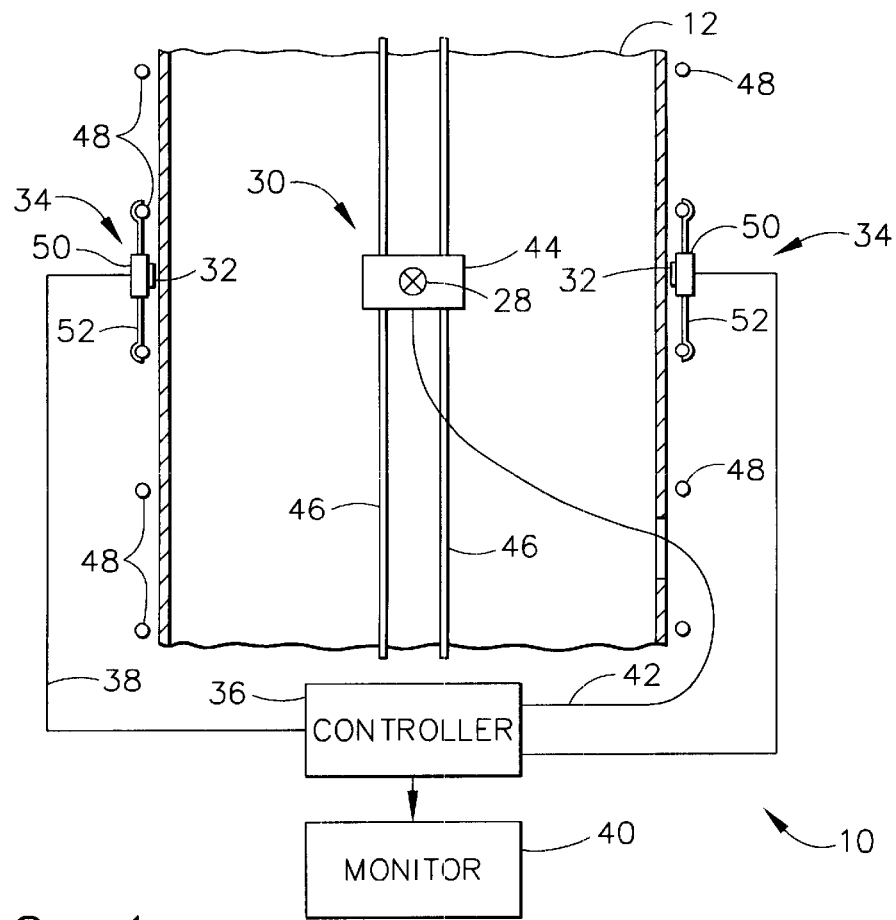
FIG. 1 is a schematic view of a radiographic inspection system for inspecting aircraft fuselages.
Figure 2:
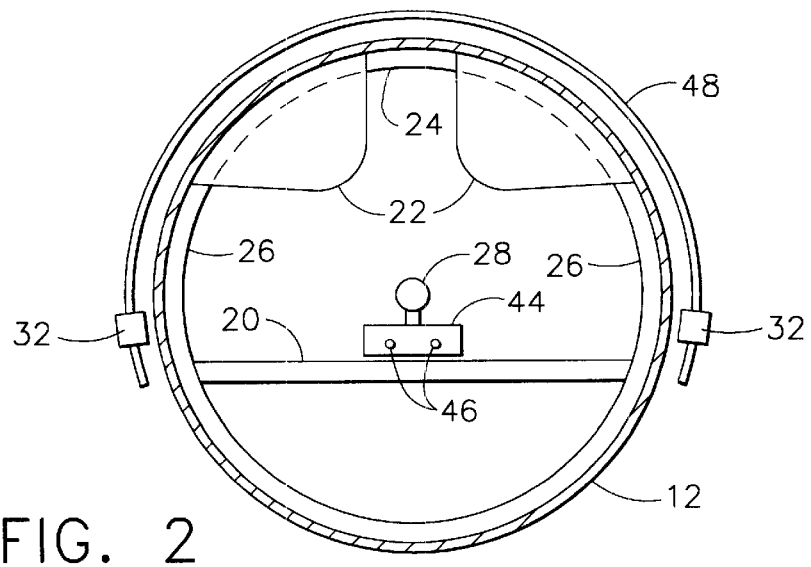
FIG. 2 is a sectional end view of a portion of the radiographic inspection system of FIG. 1.
Figure 3:
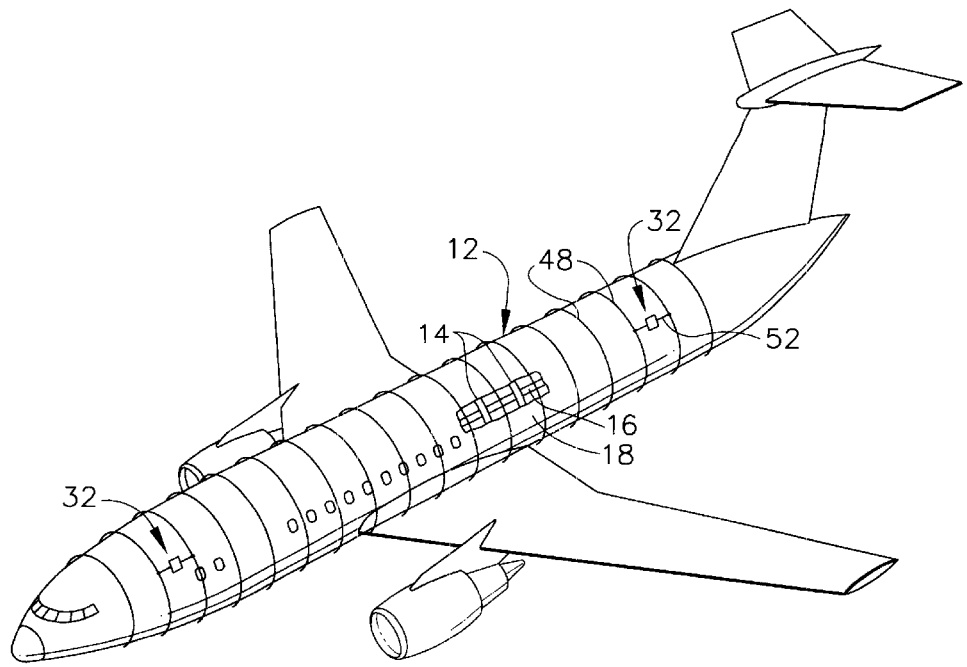
FIG. 3 is a perspective view of an aircraft equipped with the inspection system of FIG. 1 and having a portion of the fuselage shown in partial cutaway to reveal internal fuselage structure.

Referring to the drawings wherein identical reference numerals denote the same elements throughout the various views, FIGS. 1–3 schematically show a radiographic inspection system 10 for inspecting an aircraft fuselage 12. As is known in the art, the fuselage 12 generally comprises a cylindrical wall made up of a grid of circumferential frame members 14 and longitudinal stringers 16 (shown in cutaway in FIG. 3) covered by a skin 18 of lightweight sheet metal. As seen in FIG. 2, a passenger deck 20 is disposed horizontally in the fuselage 12 so as to define the floor of an interior cabin. The cabin can be provided with conventional overhead bins 22, ventilation panels 24 and side panels 26. Although not shown in the Figures, the fuselage 12 typically includes other conventional structure such as lights, wiring, insulation and the like.

The system 10 includes a radiation source 28 mounted on a source positioning system 30 located within the cabin. At least one radiation detector 32 capable of converting impinging radiation into electrical output signals is mounted on a detector positioning system 34 located outside of the fuselage 12. As will be described in more detail, the radiation source 28 and radiation detector 32 are relatively situated on opposite sides of the fuselage wall so that radiation emitted by the radiation source 28 irradiates the fuselage wall and then impinges on the radiation detector 32. Image data signals output by the radiation detector 32 are fed to a controller 36 via a cable 38. The controller 36, which can be a conventional computer unit, processes these signals and causes a corresponding image to be generated on a monitor 40. An operator is then able to view the displayed image to inspect for defects. The data image signals are also stored in a memory in the controller 36. The controller 36 is connected to the radiation source 28 via a cable 42 that passes through an opening in the fuselage 12 such as an open door. Through this connection, the controller 36 controls the operation of the radiation source 28, turning it on and off and regulating the voltage applied.

The radiation source 28 is preferably, but not necessarily, a standard industrial X-ray tube powered by a high voltage power supply (not shown). Alternative radiation sources, such as an isotopic radiation source producing gamma rays, could be used as well. The radiation source 28 produces a panoramic radiation beam in the circumferential direction of the fuselage 12, illuminating the fuselage 12 from floor line to floor line above the passenger deck 20. The radiation source 28 is positioned in the fuselage 12 by the source positioning system 30. Specifically, the source positioning system 30 includes a first carrier 44 to which the radiation source 28 is mounted. The first carrier 44 is slidingly mounted on two linear guide rails 46 that are disposed on the passenger deck 20 and extend parallel to the center longitudinal line of the fuselage 12. The first carrier 44 is moved back and forth along the guide rails 46 under the control of the controller 36. The motion is produced by any conventional motive means such as an electric motor (not shown) in a manner known in the art. Thus, the radiation source 28 can be selectively positioned along the length of the fuselage 12. The source positioning system 30 is configured to move the radiation source 28 through the desired range of motion without interference with any objects located inside the fuselage 12. Accordingly, such objects (which may include overhead bins, bulkheads, air masks, oxygen plumbing, lights, electrical wiring, fasteners, lavatory and galley fixtures, etc.) need not be removed to perform an inspection.

The detector positioning system 34 utilizes a rail system that includes a plurality of curved guide rails 48 mounted to the outer surface of the fuselage 12. Mounting can be accomplished by any means such as suction cups fixed to the rails 48 and engaging the fuselage 12. The guide rails 48 are oriented circumferentially with respect to the fuselage 12 and are spaced out along the length of fuselage 12. Each guide rail 48 is configured to match the fuselage curvature and extends from a point adjacent to the passenger deck 20 on one side of the fuselage 12, over the fuselage crown, and to a point adjacent to the passenger deck 20 on other side of the fuselage 12. The guide rails 48 are thus arranged to track the path of the panoramic radiation beam emitted by the radiation source 28. The curved guide rails 48 are situated on the fuselage 12 so as to position the radiation detector 32 over the area of interest of the fuselage 12. The radiation detector 32 is mounted between adjacent ones of the guide rails 48, and each pair of adjacent guides rails 48 defines a scanning station. The guide rails 48 are accordingly located on opposing sides of the fuselage structure to be inspected.

For example, FIG. 3 shows the guide rails 48 straddling respective ones of the frame members 14 so that they can be inspected for defects. However, it should be noted that the system 10 could also be used for inspecting other fuselage structure such as stringers, lap joints and the like. The guide rails 48 would simply be positioned accordingly.

While a single radiation detector 32 can be used on the rail system, the simultaneous use of multiple radiation detectors 32 increases the throughput of the inspection system 10. Various arrangements for multiple detectors are possible. For instance, as shown in FIGS. 1 and 2, two radiation detectors 32 can be mounted on a single scanning station, one on each side of the fuselage 12. It is also possible to simultaneously employ radiation detectors 32 at multiple scanning stations, as depicted in FIG. 3.

For each radiation detector 32, the detector positioning system 34 includes a second carrier 50 and a support beam 52 that supports the second carrier 50. The radiation detector 32 is mounted to the underside of the second carrier 50 so as to face the fuselage 12. The support beam 52 is slidingly mounted between the pair of adjacent guide rails 48 defining the selected scanning station so as to locate the radiation detector 32 at a desired location with respect to the fuselage 12. The support beam 52 is moved along the selected guide rails 48 under the control of the controller 36 by any conventional motive means in a manner known in the art. Thus, the radiation detector 32 is capable of traveling over the outer surface of the fuselage 12 above the passenger deck 20.

Figure 4:
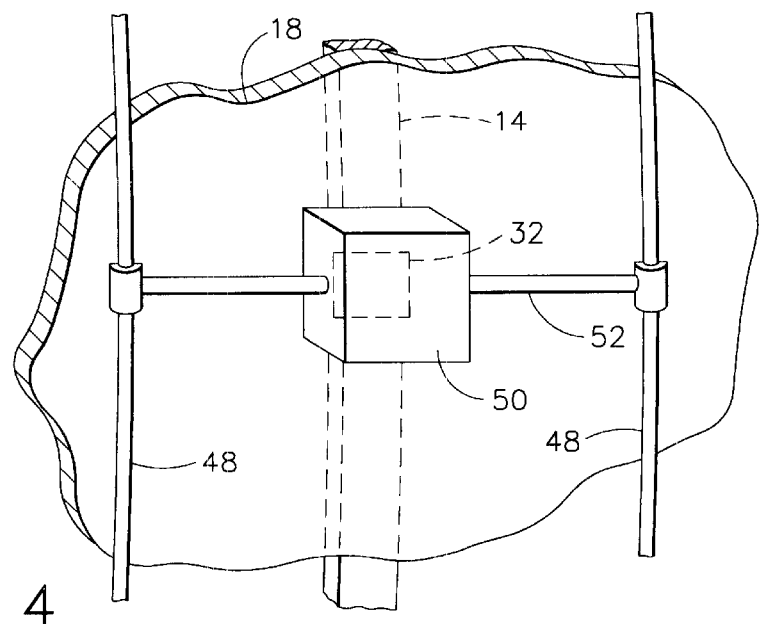
FIG. 4 is an enlarged view of a radiation detector assembly from the inspection system of FIG. 1.

As best seen in FIG. 4, the second carrier 50 (and thus the radiation detector 32) has a local lateral or longitudinal motion capability relative to the support beam 52. This lateral motion enhances the view of the frame member 14 (or whichever fuselage structure is being inspected) during an inspection. In some instances, the field of view of the vertical frame member 14 may be restricted by interior objects in the path of the radiation beams emitted by the radiation source 28. In which case, the radiation detector 32 can be laterally repositioned with respect to the frame member 14 to avoid the obstruction, thereby maintaining high image quality of the frame member 14. The lateral motion of the second carrier 50 is achieved under the control of the controller 36 in a manner known in the art. The radiation source 28 can also be finely repositioned in the longitudinal direction by the source positioning system 30.

Figure 5:
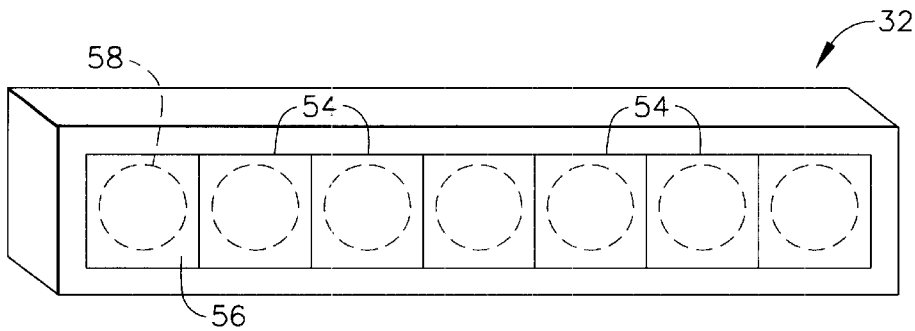
FIG. 5 is a perspective view of a linear array embodiment of a radiation detector.
Figure 6:
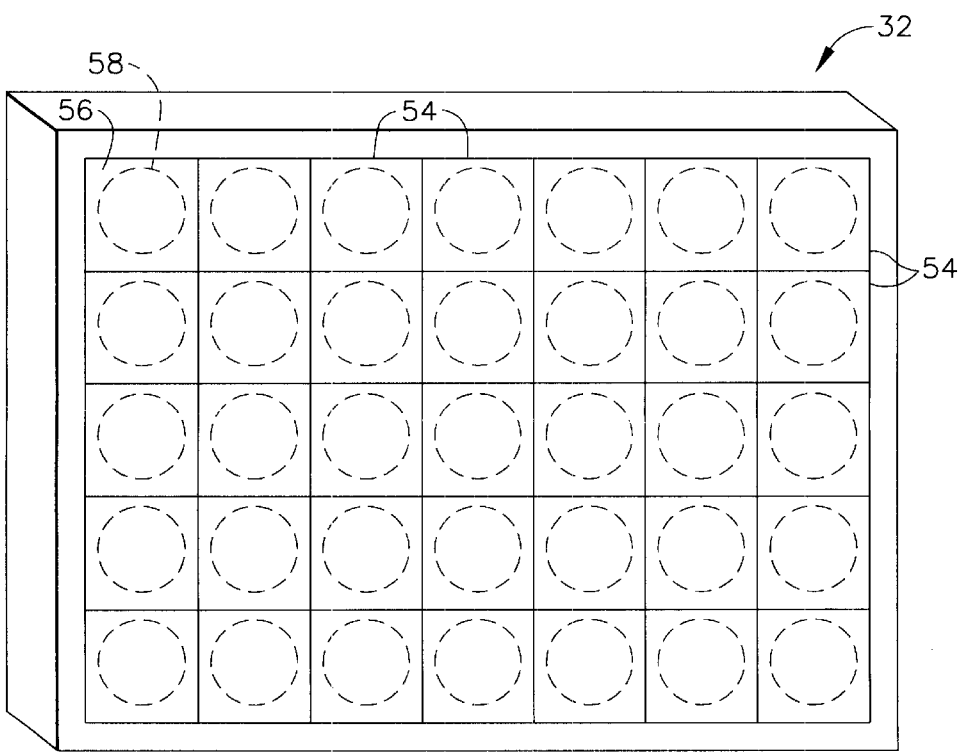
FIG. 6 is a perspective view of an area array embodiment of a radiation detector.

The radiation detector 32 can be any means that is capable of converting radiation received from the radiation source 28 into electrical output signals. Referring to FIGS. 5 and 6, one preferred type of detector is a digital X-ray detector, and many suitable detectors of this sort are commercially available. As is known in the art, digital X-ray detectors generally have an array of cells 54, each cell 54 including a layer of X-ray sensitive material 56 such as phosphor and an electronic means 58, such as a photodiode and transistor, located beneath the X-ray sensitive material 56 for producing an output signal that is indicative of the X-rays impinging on the X-ray sensitive material. The radiation detector 32 can be configured as either a linear array (FIG. 5) or an area array (FIG. 6). Either way, the array would preferably, but not necessarily, have a width of at least eight inches, although this could vary depending on the particular fuselage structure of interest. A linear array would permit a continuous scan of the fuselage 12 at each scanning station. That is, at each scanning station, the detector positioning system 34 would continuously move the radiation detector 32 over the fuselage 12, and successive lines of data would be transmitted to the controller 36. The controller 36 would then build the image one line at a time. This avoids repeated mechanical starting and stopping of the detector positioning system 34.

In operation, one or more of the radiation detectors 32 are mounted on the curved guide rails 48 of a selected scanning station. The source positioning system 30 is activated to move the radiation source 28 into longitudinal alignment with the selected scanning station. The radiation source 28 is then turned on so that the adjacent region of the fuselage 12 above the passenger deck 20 is illuminated with radiation. While the radiation source 28 is emitting radiation, the detector positioning system 34 is activated to cause the radiation detector or detectors 34 to travel over the outer surface of the fuselage 12. If one radiation detector is employed, then it travels the over the entire distance of the guide rails 48, up one side of the fuselage 12, over the crown and down the other side. If two radiation detectors 32 are employed at the scanning station, then each one travels up an opposing side of the fuselage 12, meeting at the crown. Radiation emitted by the radiation source 28 passes through the fuselage 12 and impinges on each radiation detector 32. The radiation is converted into electrical signals that are fed to the controller 36. The controller 36 processes these signals and generates images that are displayed on the monitor 40. An operator inspects the images for defects.

Once the inspection of the fuselage 12 at the first scanning station is completed, the radiation detectors 32 are moved to the next scanning station, and the source positioning system 30 again moves the radiation source 28 into longitudinal alignment. The inspection at this scanning station is then carried out in the same manner with the radiation detectors 32 being moved over the outer surface of the fuselage while the radiation source 28 is turned on. This process is repeated for each scanning station until the entire fuselage 12 has been inspected. As mentioned above, radiation detectors 32 can be simultaneously employed at multiple scanning stations to decrease the overall time needed to inspect the entire fuselage 12. This approach would require an equal number of radiation sources 28 located in the fuselage 12. One preferred embodiment would be to start inspections at opposite ends of the fuselage 12 and move toward the center.

In the above description, the radiation source 28 is located inside of the fuselage 12 and the radiation detector or detectors 32 are located outside of the fuselage 12. This arrangement is generally best for image resolution because the radiation detectors 32 can be located fairly close to the fuselage structure being inspected, thereby minimizing the magnification effect. Excessive magnification of the images can result in degradation of image resolution. On the other hand, some magnification would be helpful in inspecting the images and is thus desirable. Some commercially available X-ray tubes have built-in magnification capability. The system 10 could also include a separate magnification element located between the radiation source 28 and the radiation detector 32. Furthermore, the system 10 can be alternatively configured so that the radiation source 28 is located outside and the radiation detectors 32 are located inside of the fuselage 12. Locating the radiation detectors inside of the fuselage 12 will generally place them farther away from the fuselage structure being inspected. A microfocus tube could be used to compensate for excessive magnification that may result from this arrangement.

Figure 7:
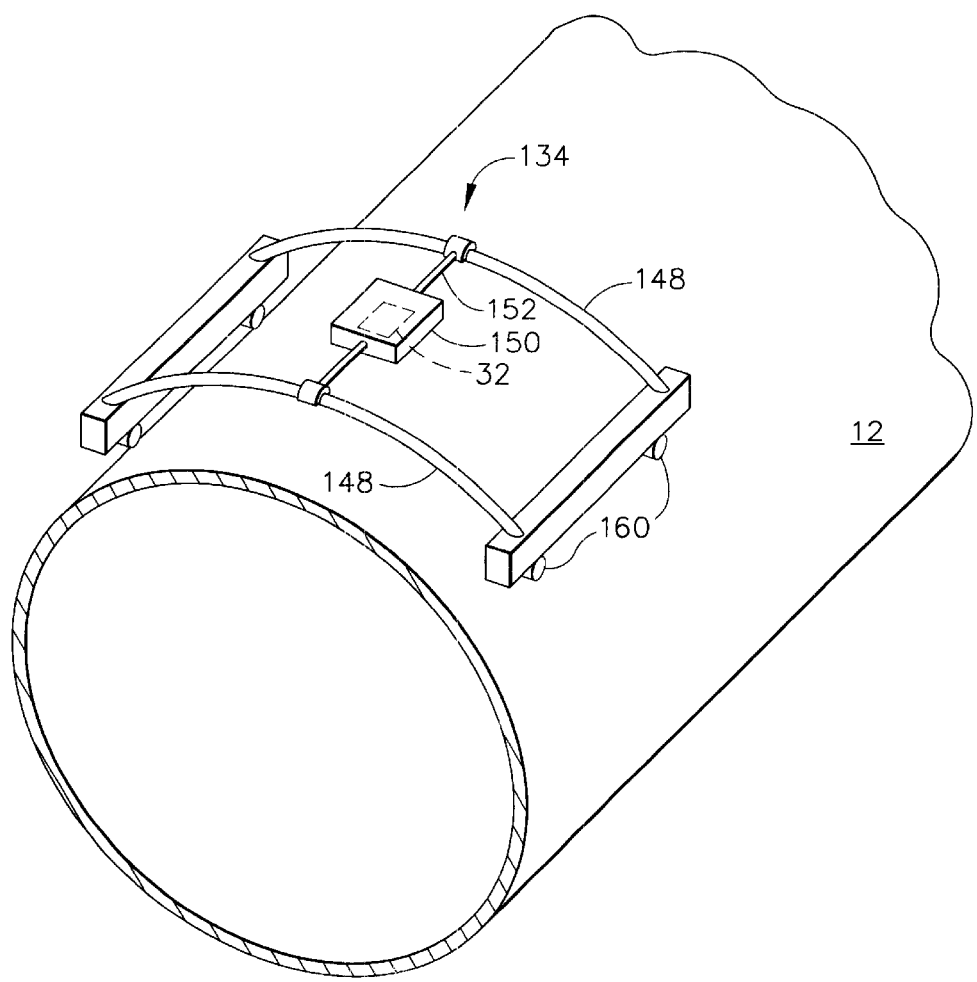
FIG. 7 is a perspective view of an aircraft equipped with an inspection system having an alternative detector positioning system.

Referring now to FIG. 7, an alternative detector positioning system 134 is shown. The alternative detector positioning system 134 utilizes a rail trolley system that has remote longitudinal positioning capability to move to successive scanning stations in coordination with the radiation source. The system 134 includes two curved guide rails 148 mounted on wheels 160 over the crown of the fuselage 12. The guide rails 148 are oriented circumferentially with respect to the fuselage 12 and are spaced apart longitudinally. The detector positioning system 134 further includes a second carrier 150 and a support beam 152 that supports the second carrier 150. The support beam 152 is slidingly mounted between the guide rails 148. The radiation detector 32 is mounted to the underside of the second carrier 150 so as to face the fuselage 12. The support beam 152 is moved along the guide rails 148 under the control of the controller 36 by any conventional motive means in a manner known in the art. This moves the radiation detector 32 circumferentially over the outer surface of the fuselage 12. As in the first embodiment, the second carrier 150 (and thus the radiation detector 32) has a local lateral or longitudinal motion capability relative to the support beam 152. This lateral motion enhances the view of the frame member 14 (or whichever fuselage structure is being inspected) during an inspection.

A motive means such as an electric motor (not shown) is provided to drive the wheels 160 under the control of the controller 136 in a manner known in the art to thereby move the curved guide rails 148 longitudinally along the fuselage 12. Thus, the radiation detector 32 can be positioned at the selected scanning station as the radiation source is positioned inside the cabin. Exact longitudinal alignment of the radiation detector 32 with the radiation source 28 is not required because the width of the radiation beam emitted by the radiation source will generally cover both sides of the frame member 14. Furthermore, the radiation detector position can be adjusted by moving the second carrier 150 relative to the support beam 152 prior to the circumferential scan.

The foregoing has described a radiographic inspection system 10 that provides high speed digital inspection of aircraft fuselages. The system 10 allows for inspection without removal of interior bins, panels, insulation, lights and wiring, thereby realizing substantial time and cost savings over traditional inspection practices. The system 10 can also stage other nondestructive testing (NDT) sensors so that other NDT modalities can be performed simultaneously with the radiographic inspection, thereby further enhancing productivity. For example, an ultrasonic probe could be mounted onto one of the positioning systems to inspect along the longitudinal direction at lap joints and stringers for corrosion and cracking of fasteners.

While specific embodiments of the present invention have been described, it will be apparent to those skilled in the art that various modifications thereto can be made without departing from the spirit and scope of the invention as defined in the appended claims.

What is claimed is:

1. A system for radiographic inspection of an aircraft fuselage, said system comprising:
    a radiation source and a radiation detector, one of said source and said detector being located inside of said fuselage, and the other of said source and said detector being located outside of said fuselage, said radiation detector being aligned with said radiation source longitudinally along said fuselage;
    first positioning means for moving one of said radiation source and said radiation detector longitudinally with respect to said fuselage; and
    second positioning means for moving the other one of said radiation source and said radiation detector circumferentially with respect to said fuselage.

2. The system of claim 1 wherein said first positioning means comprises at least one guide rail disposed inside said fuselage and extending longitudinally with respect to said fuselage and a carrier slidingly mounted on said guide rail, said one of said radiation source and said radiation detector being mounted on said carrier.

3. The system of claim 1 wherein said second positioning means comprises at least two guide rails mounted to an outer surface of said fuselage and a carrier slidingly mounted between said two guide rails, said other one of said radiation source and said radiation detector being mounted on said carrier.

4. The system of claim 3 wherein said second positioning means further comprises a support beam slidingly mounted to said two guide rails, said carrier being slidingly mounted to said support beam to enable longitudinal motion with respect to said fuselage.

5. The system of claim 3 wherein said two guide rails are capable of moving longitudinally with respect to said fuselage.

6. The system of claim 1 wherein said radiation source is located inside of said fuselage and said radiation detector is located outside of said fuselage, said first positioning means moving said radiation source and said second positioning means moving said radiation detector.

7. The system of claim 6 wherein said first positioning means comprises at least one guide rail disposed inside said fuselage and extending longitudinally with respect to said fuselage and a carrier slidingly mounted on said guide rail, said radiation source being mounted on said carrier.

8. The system of claim 6 wherein said second positioning means comprises at least two guide rails mounted to an outer surface of said fuselage and a carrier slidingly mounted between said two guide rails, said radiation detector being mounted on said carrier.

9. The system of claim 8 wherein said second positioning means further comprises a support beam slidingly mounted to said two guide rails, said carrier being slidingly mounted to said support beam to enable longitudinal motion with respect to said fuselage.

10. The system of claim 8 wherein said two guide rails are capable of moving longitudinally with respect to said fuselage.

11. The system of claim 1 further comprising at least one additional radiation detector.

12. The system of claim 11 further comprising at least one additional radiation source.

13. The system of claim 1 further comprising a controller for controlling said first and second positioning means.

14. The system of claim 13 wherein said controller receives image data signals from said radiation detector.

15. The system of claim 14 further comprising a monitor for displaying images generated by said image data signals.

16. The system of claim 1 wherein said radiation source is an X-ray source and said radiation detector is an X-ray detector.

17. A system for radiographic inspection of an aircraft fuselage, said system comprising:

a radiation source located inside of said fuselage;

a radiation detector located outside of said fuselage, said radiation detector being aligned with said radiation source longitudinally along said fuselage;

a source positioning system for moving said radiation source longitudinally with respect to said fuselage; and a detector positioning system for moving said radiation detector circumferentially with respect to said fuselage.

18. The system of claim 17 wherein said source positioning system comprises at least one guide rail disposed inside said fuselage and extending longitudinally with respect to said fuselage and a carrier slidingly mounted on said guide rail, said radiation source being mounted on said carrier.

19. The system of claim 17 wherein said detector positioning system comprises at least two guide rails mounted to an outer surface of said fuselage and a carrier slidingly mounted between said two guide rails, said radiation detector being mounted on said carrier.

20. The system of claim 19 wherein said detector positioning system further comprises a support beam slidingly mounted to said two guide rails, said carrier being slidingly mounted to said support beam to enable longitudinal motion with respect to said fuselage.

21. The system of claim 19 wherein said two guide rails are capable of moving longitudinally with respect to said fuselage.

22. The system of claim 17 further comprising at least one additional radiation detector located outside of said fuselage.

23. The system of claim 22 further comprising at least one additional radiation source located inside of said fuselage.

24. The system of claim 17 further comprising a controller for controlling said first and second positioning means.

25. The system of claim 24 wherein said controller receives image data signals from said radiation detector.

26. The system of claim 25 further comprising a monitor for displaying images generated by said image data signals.

27. The system of claim 17 wherein said radiation source is an X-ray source and said radiation detector is an X-ray detector.

28. A method for radiographic inspection of an aircraft fuselage, said method comprising:

providing a radiation source inside of said fuselage;

providing a radiation detector outside of said fuselage, said radiation detector being aligned with said radiation source longitudinally along said fuselage; and causing said radiation detector to move over said fuselage in a circumferential direction while said radiation source is illuminating an adjacent region of said fuselage with radiation.

29. The method of claim 28 further comprising:

subsequently moving said radiation source and said radiation detector to a different longitudinal location with respect to said fuselage; and then causing said radiation detector to move over said fuselage in a circumferential direction while said radiation source is illuminating an adjacent region of said fuselage with radiation.

30. The method of claim 28 further comprising:

collecting image data signals from said radiation detector; and displaying images generated by said image data signals.

* * * * *